(12) United States Patent
Picard et al.

(10) Patent No.: US 10,390,802 B1
(45) Date of Patent: Aug. 27, 2019

(54) EYESCAN APP FOR DETECTING IMPAIRMENT

(71) Applicants: Christopher L. Picard, Billings, MT (US); John T. Thebo, Payette, ID (US); Craig T. Thebo, Payette, ID (US)

(72) Inventors: Christopher L. Picard, Billings, MT (US); John T. Thebo, Payette, ID (US); Craig T. Thebo, Payette, ID (US)

(*) Notice: Subject to any disclaimer, the term of this patent is extended or adjusted under 35 U.S.C. 154(b) by 40 days.

(21) Appl. No.: 15/209,664

(22) Filed: Jul. 13, 2016

Related U.S. Application Data

(60) Provisional application No. 62/191,946, filed on Jul. 13, 2015.

(51) Int. Cl.
*A61B 10/00* (2006.01)
*A61B 3/14* (2006.01)
*A61B 3/11* (2006.01)
*A61B 3/00* (2006.01)

(52) U.S. Cl.
CPC ............ *A61B 10/00* (2013.01); *A61B 3/0025* (2013.01); *A61B 3/112* (2013.01); *A61B 3/145* (2013.01); *A61B 2010/0009* (2013.01)

(58) Field of Classification Search
None
See application file for complete search history.

*Primary Examiner* — Jack Dinh
(74) *Attorney, Agent, or Firm* — Plager Schack LLP

(57) ABSTRACT

A system and software application are disclosed for detecting impairment of person under the influence of drugs and/or alcohol. The system may scan the person's eye(s) and measure the pupil for excessive dilation. The system may also record eye movement and check for nystagmus of the eye that indicates the person is under the influence of alcohol.

4 Claims, 2 Drawing Sheets

EYESCAN APP FOR DETECTING IMPAIRMENT

This application claims priority to provisional patent application U.S. Ser. No. 62/191,946 filed on Jul. 13, 2015, the entire contents of which, including drawings and a specification are herein incorporated by reference.

BACKGROUND

The embodiments herein relate generally to applications for detecting impairment.

Currently, there is very little readily available for law enforcement and the general consumer to detect whether someone is impaired by alcohol or narcotics. Law enforcement, for example must rely on field testing and chemical testing to determine if an individual is impaired by alcohol. Parents do not currently have a consumer product to use to test their children As can be seen, there is a need for a system that uses readily available technology to provide testing for impairment.

SUMMARY

In one aspect of the disclosure, a computer program product for testing impairment in an individual comprises a non-transitory computer readable storage medium having computer readable program code embodied therewith. The computer readable program code is configured to, when executed by a processor: capture, via a camera of a mobile computing device, an image of a person's eye; measure a pupil size of the person's eye from the captured image; compare the measured pupil size to a stored threshold pupil size; determine whether the measured pupil size exceeds the threshold pupil size; and provide an electronic report indicating whether the person is impaired based on the determination of determine whether the measured pupil size exceeds the threshold pupil size.

In another aspect, a computer program product for testing impairment in an individual comprises a non-transitory computer readable storage medium having computer readable program code embodied therewith. The computer readable program code is configured to, when executed by a processor: capture a moving image file of a person's eye through a video recorder of a mobile electronic computing device; record, by a processor in the mobile electronic computing device, an amount of nystagmus of the person's eye from the captured moving image file; analyze the recorded amount of nystagmus of the person's eye from the captured moving image file for lack of control; and provide an electronic report indicating whether the person is impaired based on the analyzed recorded amount of nystagmus for signs of impairment.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Broadly, embodiments of the subject technology provide a system that may test for and determine impairment of an individual because of, for example, drugs or alcohol. The need for aspects of the subject technology may be particular useful in states that have legalized recreational drug use. Conventional drug testing costs between $30.00 and $125.00 per test and can be higher depending on the test, plus the costs of employees administering the test.

As of 31 Mar. 2013 there were 129,584 full-time equivalent (FTE) police officers in the 43 police forces of England and Wales. This is a decrease of 3.4% or 4,516 officers (FTE) compared with 31 Mar. 2012. Jul. 18, 2013. Over 20,000,000 drug related workplace accidents occur a year. Psychoactive substance use poses a significant threat to the health, social and economic fabric of families, communities and nations. The extent of worldwide psychoactive substance use is estimated at 2 billion alcohol users, 1.3 billion smokers and 185 million drug users.

Figure 1:
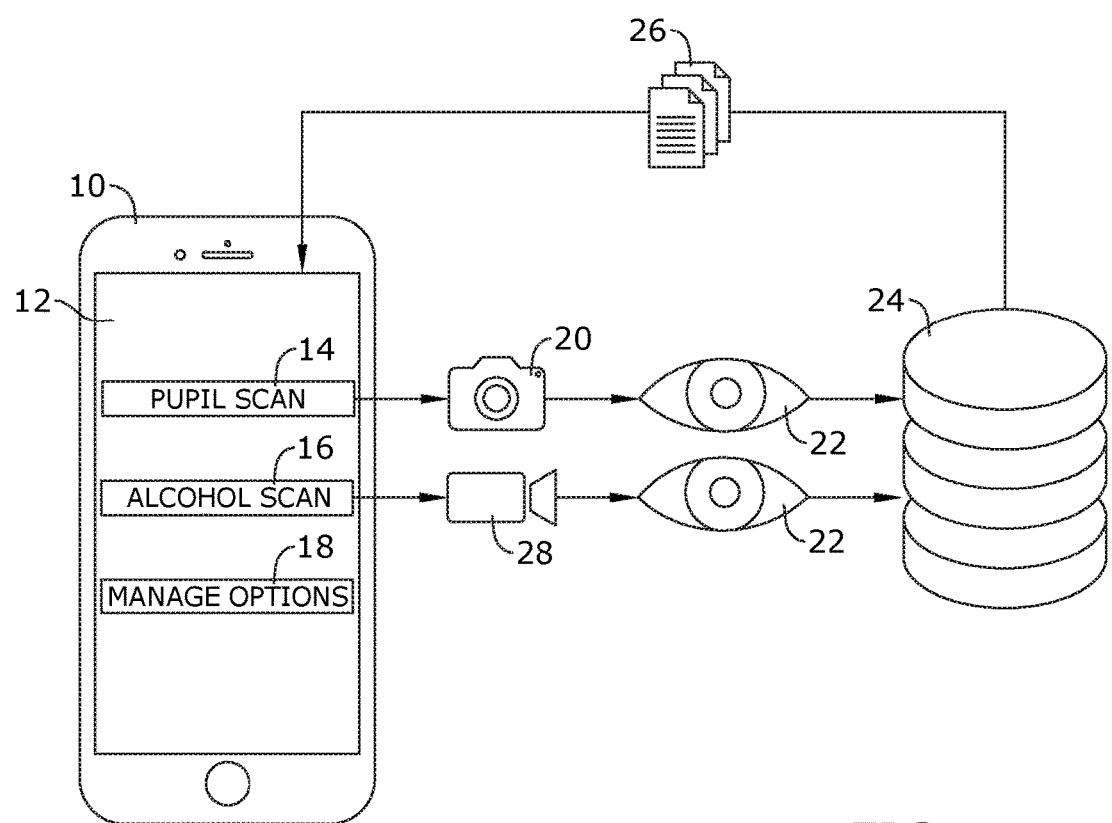
FIG. 1 is a block diagram of a system for detecting impairment through an eye scan in accordance with an exemplary embodiment of the subject disclosure.

Referring to FIG. 1, a system for detecting impairment through an eye scan is shown according to an embodiment. In an example context, the end user may be a police officer administering a test for impairment to a subject under suspicion of impairment. An exemplary embodiment of the subject technology may be in the form of a software application usable by end users via a mobile electronic computing device 10 (referred to sometimes as the "device 10"). A user interface 12 displays options to perform a pupil scan 14, an alcohol scan 16, or manage user options 16. The tests for pupil scan 14 may capture a still image of the person's eye(s) 22 using a still camera 20 integrated into the device 10. The alcohol scan 16 initiates a scan of a person's eye(s) 22 via a video recorder 28 to record and measure ocular features and reactions to the scan. The results of the pupil scan 14 and/or alcohol scan 16 are sent to a remote server 24 for analysis and a report 26 of results are transmitted back to the device 10. The scan may occur in approximately three seconds. As will be appreciated, the testing and results are near immediate. Various user options and test features may be available per the following headings:

Pupil Scan:

Recreational drug use: Certain drugs can cause the pupils to dilate or constrict abnormally. A dilated pupil results from contraction of the dilator muscle or relaxation of the iris sphincter. Dilation may occur normally in dim illumination, or may be produced by certain drugs (mydriatics, cycloplegics). Normal pupil size tends to range between 2.0 and 5.0 mm depending on the lighting. A pupil measurement of 5.1 mm or greater may be an indication that the person is under the influence of recreational drugs. The pupil size remains above 5.1 mm for several hours, whereas someone that has not been using recreational drug will be smaller than 5.0 mm.

Alcohol Scan:

Horizontal Gaze Nystagmus: This term refers to the involuntary jerking of the eye that occurs naturally when the eye gazes to the side. But this jerking (or nystagmus) is exaggerated when someone is impaired by alcohol. Manually, officers look for three indicators of impairment in each eye: inability to follow a moving object smoothly; distinct eye jerking when eye is at maximum deviation; and eye-jerking within 45 degrees of center. Nystagmus is an involuntary jerking or bouncing of the eyeball that occurs when there is a disturbance of the vestibular (inner ear) system or the oculomotor control of the eye. Embodiments of the subject technology may record movement of the eyeball in a moving image so that nystagmus can be analyzed. Horizontal gaze nystagmus (HGN) refers to a lateral or horizontal jerking when the eye gazes to the side. In the impaired driving context, alcohol consumption or consumption of certain other central nervous system depressants, inhalants or phencyclidine, hinders the ability of the brain to correctly control eye muscles, therefore causing the jerk or bounce associated with HGN. As the degree of impairment becomes greater, the nystagmus, becomes more pronounced. This is assessed in the horizontal gaze nystagmus test. HGN is at reliable and effective indicator of alcohol impairment and that ample evidence is available to prove that reliability.

In some embodiments, a central server 26 may receive the data from the eye scan and determine whether the measured/recorded data indicates dilated pupils or overactive nystagmus indicated of impairment by drugs or alcohol. In some embodiments, collected data may be sent to a person(s) at a database center and is not limited to just a database, server and/or website. By studying and analyzing the information sent to be analyzed and then returned to the operator of the mobile device.

Figure 2:
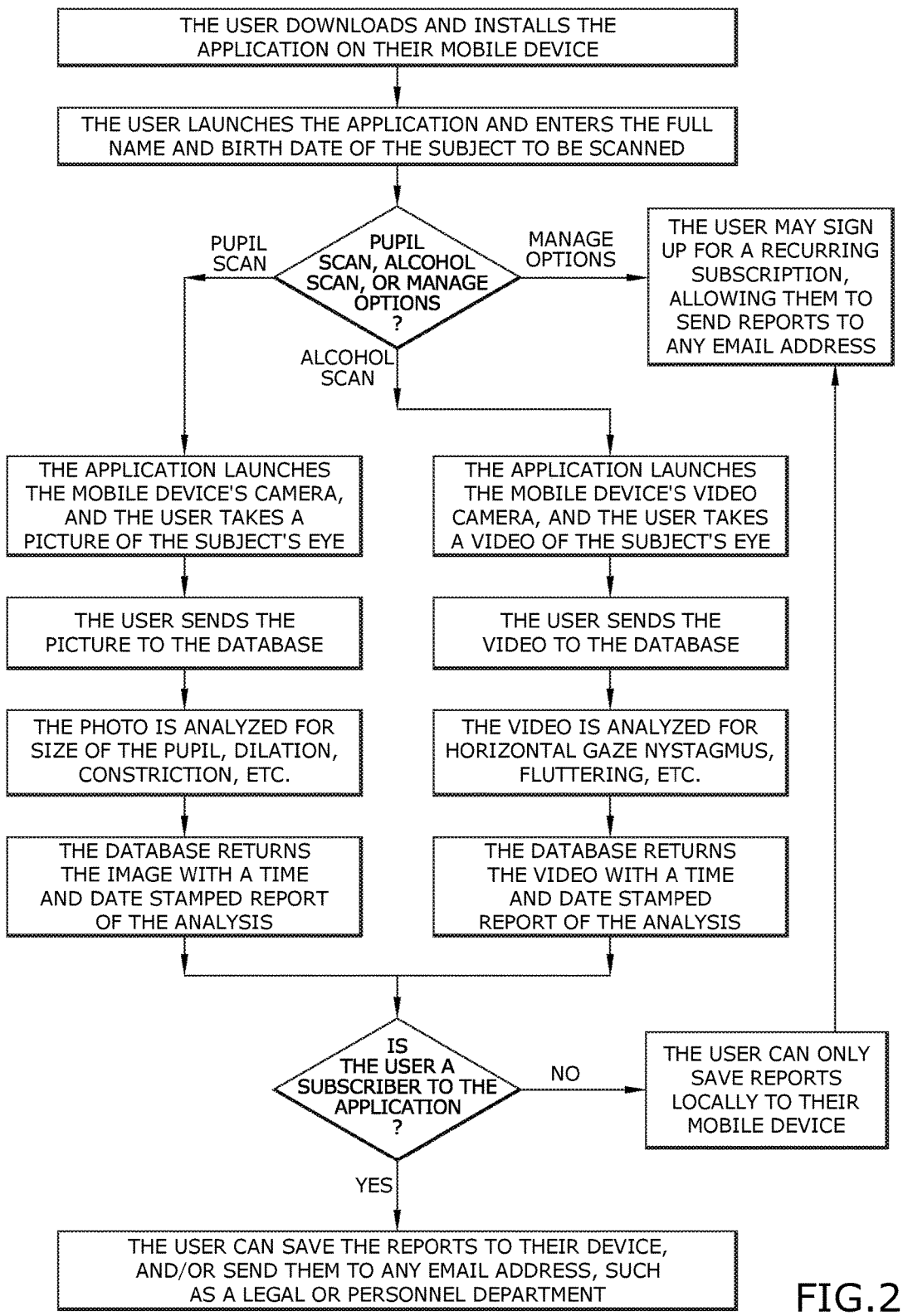
FIG. 2 is a flowchart of a method of detecting impairment through an eye scan in accordance with an exemplary embodiment of the subject disclosure.

Referring now to FIG. 2, a method for detecting impairment through an eye scan through a mobile computing device is shown. The user may download a software embodiment of the technology to a mobile computing device that includes a camera and/or video recorder and is radio enabled to transmit and receive data. Upon launching the application, the subject's biographical data may be entered to be attached to a test he or she is subjected to. From a user interface, the user selects a function: pupil scan, alcohol scan, or manage options.

The Pupil Scan Button:

In response to selection of a pupil scan, the camera of the electronic mobile device is activated. The user (operator) will focus in on the eye (pupil) of the subject being scanned and take a picture. The user (operator) of the mobile device will then push send. This will automatically send the picture of the pupil to the database where it will be analyzed for size of the dilated pupil. Analysis may be sent back to the mobile device of the scan on which it was done on. The user (operator) of the app will receive a time stamped and date stamped result of the image analysis as well as the image of the scan that was just performed as a record to keep for their records.

The Alcohol Scan Button:

The Alcohol scan function will activate the video recorder of the mobile device. The video camera on the device will be used and will record the fluttering of the eye at the farthest left and the furthest right of each eye, (when the eye is at its farthest to the right or left and someone has been consuming alcohol, it causes the eye to have a fluttering reaction when it is forced to stay in the outer corner of "farthest right or left of the eye socket" after recording the operator push send and the information will be sent to the database where it will be analyzed and sent back to the operator of the device and they will receive a time stamp, a date stamp, of the results of the image as well as the image of the scan it just performed on the video giving the user (operator) information to determining if the individual has consumed too much alcohol.

The application may determine if the user is a subscriber. Subscribers may save test results to the mobile device and/or send them through for example, e-mail to a remote storage unit. Non-subscribers may be limited to storing results on the device administering the scan. In some embodiments, the user interface may provide a manage screen option that is configured to assist in signing the user up for a subscription.

As will be appreciated, other applications outside of law enforcement can benefit from the subject technology. Large and small companies will be able to test all employees on a regular basis for drug or alcohol use in the workplace making it a safe environment for all of their employees and customers, saving the company time and money on drug testing. Companies will be able to test any employee within minutes and be able to determine if their employee is using an illegal substance or alcohol without having to send the employee to be tested, wasting company time while employee is away from the work site. This is important in many fields such as the medical field, transportation and carriers, etc.

Police officers and parole and probation officers will be able to utilize the subject technology giving them probable cause to make an arrest, issue a citation as well as evidence to us in court and/or as a legal visual document. Departments would also be able to test their officers as well.

Establishments that serve alcohol such as restaurants and bars will be able to scan their customers upon customer consent if they feel that customer has had too much to drink and would impair their driving. This would reduce drunk driving accidents as well as fatalities and accidents with other motor vehicles.

Parents including single mothers and single fathers, grandparents or family members would be able to test their children at any time they please. Families would be able to get help for their child or children for substance abuse before it escalated and before their child or children get into trouble with the law, or pass away due to an overdose or be involved in a fatal accident.

The subject technology will also be able to be used by friends that are having a party, wedding or special event where people are drinking. The host or concerned friend would be able to scan them before they leave the party or event, saving their life, the other people the car with them and/or an innocent bystanders.

The mobile computing device 10 and server 26 may be general purpose computing devices which may include, but are not limited to, one or more processors or processing units, a system memory, and a bus that couples various system components including the system memory to the processor as is known in the art of computers. The mobile computing device 10 and server 26 may be described in the general context of computer system executable instructions, such as program modules, being executed by a computer system (described for example, below). In some embodiments, the server 26 may be a cloud computing node connected to a cloud computing network (not shown) and practiced in distributed cloud computing environments where tasks are performed by remote processing devices that are linked through a communications network. In a distributed cloud computing environment, program modules may be located in both local and remote computer system storage media including memory storage devices.

The mobile computing device 10 and server 26 may typically include a variety of computer system readable media. Such media includes non-transitory, volatile and non-volatile media, removable and non-removable media. The system memory could include one or more computer system readable media in the form of volatile memory, such as a random access memory (RAM) and/or a cache memory. By way of example only, a storage system can be provided for reading from and writing to a non-removable, non-volatile magnetic media device. The system memory may include at least one program product having a set (e.g., at least one) of program modules that are configured to carry out the functions of embodiments of the invention. The program product/utility, having a set (at least one) of program modules, may be stored in the system memory by way of example, and not limitation, as well as an operating system, one or more application programs, other program modules, and program data. Each of the operating system, one or more application programs, other program modules, and program data or some combination thereof, may include an implementation of a networking environment. The program modules generally carry out the functions and/or methodologies of embodiments of the invention as described above by aid of a processing unit.

The mobile computing device 10 and server 26 may also communicate with one or more devices such as a keyboard, a pointing device, display, etc.; and/or any devices (e.g., network card, modem, etc.) that enable the mobile computing device 10 or server 26 to communicate with one or more other computing devices. Such communication can occur via Input/Output (I/O) interfaces. Alternatively, the mobile computing device 10 and server 26 can communicate with one or more networks such as a local area network (LAN), a general wide area network (WAN), and/or a public network (e.g., the Internet) via a network adapter.

As will be appreciated by one skilled in the art, aspects of the disclosed invention may be embodied as a system, method or process, or computer program product. Accordingly, aspects of the disclosed invention may take the form of an entirely hardware embodiment, an entirely software embodiment (including firmware, resident software, microcode, etc.) or an embodiment combining software and hardware aspects that may all generally be referred to herein as a "circuit," "module," or "system." Furthermore, aspects of the disclosed invention may take the form of a computer program product embodied in one or more computer readable media having computer readable program code embodied thereon.

Any combination of one or more computer readable media (for example, storage system) may be utilized. In the context of this disclosure, a computer readable storage medium may be any tangible or non-transitory medium that can contain, or store a program (for example, the program product) for use by or in connection with an instruction execution system, apparatus, or device. A computer readable storage medium may be, for example, but not limited to, an electronic, magnetic, optical, electromagnetic, infrared, or semiconductor system, apparatus, or device, or any suitable combination of the foregoing.

Aspects of the disclosed invention are described above with reference to block diagrams of methods, apparatus (systems) and computer program products according to embodiments of the invention. It will be understood that each block of the block diagrams, and combinations of blocks in the flowchart illustrations and/or block diagrams, can be implemented by computer program instructions. These computer program instructions may be provided to the processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above. Also, the addition of powered sub-woofers to augment an embodiment will not invalidate the claims of this invention.

What is claimed is:

1. A computer program product for testing impairment in an individual, the computer program product comprising a non-transitory computer readable storage medium having computer readable program code embodied therewith, the computer readable program code being configured to, when executed by a processor:
   initiate a test for impairment of a person in response to a button press of a user interface on a mobile computing device;
   capture in response to the button press of the user interface, via a camera of the mobile computing device, an image of the person's eye;
   record ocular features in the captured image;
   measure a pupil size of the person's eye from the recorded ocular features in the captured image;
   compare the measured pupil size to a stored threshold pupil size value;
   determine whether the measured pupil size exceeds the threshold pupil size value; and
   provide an electronic report indicating whether the person is impaired based on the determination of determine whether the measured pupil size exceeds the threshold pupil size value.

2. The computer program product of claim 1, wherein the measured pupil size is analyzed by a remote server.

3. The computer program product of claim 2, wherein the electronic report is transmitted from the remote server to the mobile computing device for display.

4. The computer program product of claim 3, wherein the electronic report includes a time stamp, a date stamp, and the captured image.

\* \* \* \* \*